United States Patent [19]

Klaveness et al.

[11] Patent Number: 5,354,549
[45] Date of Patent: Oct. 11, 1994

[54] IODINATED ESTERS

[75] Inventors: Jo Klaveness, Skoyen Terrasse; Per Strande, Nordengveien, both of Norway

[73] Assignee: Nycomed Imaging AS, Oslo, Norway

[21] Appl. No.: 802,529

[22] Filed: Dec. 5, 1991

Related U.S. Application Data

[63] Continuation of Ser. No. 458,631, Jan. 18, 1990, abandoned.

[30] Foreign Application Priority Data

Jul. 24, 1987 [GB] United Kingdom .................. 8717625

[51] Int. Cl.$^5$ ...................... A61K 49/04; A61K 49/00
[52] U.S. Cl. ........................................... 424/5; 424/4; 424/9
[58] Field of Search ..................... 424/4, 5, 9

[56] References Cited

U.S. PATENT DOCUMENTS 4,567,034  1/1986  Charles et al. ........................ 424/5

FOREIGN PATENT DOCUMENTS 0300828  1/1989  European Pat. Off. .
2230377 12/1974  France .
0866184  4/1961  United Kingdom .
2157283 10/1985  United Kingdom .

OTHER PUBLICATIONS

*Handbook of Experimental Pharmacology*, vol. 73: "Radio Contrast Agents" edited by M. Sovak, published by Springer–Verlag, Berlin, 1984.
Chemical Abstracts (83: 48224s) 1975.
Chemical Abstracts (84: 79731e) 1976.
Chemical Abstracts (105: 208607x) 1986.
Chemical Abstracts (111: 57290j) 1989.

*Primary Examiner*—Marianne M. Cintins
*Assistant Examiner*—K. Weddington
*Attorney, Agent, or Firm*—Bacon & Thomas

[57] ABSTRACT

The invention relates to metabolically labile water-insoluble esters of formula (I), wherein $R^1$ is an aliphatic, araliphatic, aryl or heterocyclic group; $R^2$ is hydrogen or an aliphatic, aryl or araliphatic group; $R^3$ is as defined for $R^1$, or $R^3$ and $R^2$ together form an alkylene chain; the molecule containing at least one iodine atom and being metabolised to form products which are soluble in body fluids. The esters are used in X-ray and ultrasound image enhancement.

7 Claims, No Drawings

IODINATED ESTERS

This application is a continuation of application Ser. No. 07/458,631, filed Jan. 18, 1990; now abandoned.

The present invention relates to contrast agents for medical X-ray and ultrasound imaging and to their preparation and use.

It has been proposed to improve the detection of lesions in the liver and spleen by the use of contrast agents which accumulate in these organs. A number of substances have been suggested but there is no such product on the market at the present time and each of the contrast agents so far proposed has some disadvantages.

Since the reticuloendothelial system of the liver and spleen is well known to trap particles by phagocytosis, contrast agents in particulate form are particularly well adapted for visualisation of these organs. Emulsions of iodinated oils have been proposed in this context, particularly iodinated ethyl esters of poppy seed oil. (Vermess, M., et al, Radiology, 137 (1980) 217). However, these substances have proved unduly toxic.

Another possibility is to use liposomes containing water soluble iodinated contrast agents. (Havron A. et al, Radiology, 140 (1981) 507). However, since only a limited amount of iodine can be incorporated in each liposome, it is necessary to administer relatively large amounts of lipids in order to attain adequate contrast enhancement. This tends to cause emboli in the lung capillaries. Furthermore, liposomes have been found to be relatively unstable on storing (Shulkin, P. M., et al, J. Microencapsul., 1 (1984) 73).

Submicron thorium dioxide particles have been used for liver visualisation and have shown effective enhancement of contrast in clinical testing but their use has been discontinued because of the extremely lengthy retention of the particles in the liver. This, in combination with the inherent radioactivity of thorium, has led to serious adverse side effects, including neoplasm and fibrosis. (Thomas, S. F., Radiology, 78 (1962) 435).

It has also been proposed to use particles comprising the ethyl ester of the water soluble X-ray contrast agent, iodipamide (Violante, M. R., et al, Invest. Radiol., 2, (1984) 133). However, ethyl esters are not sufficiently metabolically labile and thus would be expected to be retained in the liver for a considerable period. Indeed, both this ester and an iodinated ethyl ester of poppy seed oil gave an increase in lipid vacuoles in the hepatocytes after intravenous administration. (Vermess et al, Radiology, 137 (1980) 217) and Violante M. R., Invest. Radiol., 2 (1984) 133). Such morphological changes indicate an adverse effect on the hepatocytes.

We have now found that particularly useful contrast agents for the visualisation of the liver and spleen comprises particulate lipophilic iodine-containing esters which are metabolically labile to form water-soluble substances which are substantially non-toxic and are not retained in the target organs.

According to the present invention we provide metabolically labile water-insoluble iodinated esters of the formula (I):

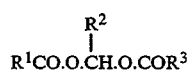

in which
$R^1$ is a substituted or unsubstituted $C_{1-20}$ aliphatic, $C_{7-20}$-araliphatic or $C_{6-20}$ aryl group or a $C_{1-20}$ heterocyclic group having one or more hetero atoms selected from O, S and N;

$R^2$ is hydrogen or a substituted or unsubstituted aliphatic, aryl or araliphatic group; and $R^3$ is a group as defined above for $R^1$, which may be the same as or different from $R^1$, or $R^2$ and $R^3$ together represent a substituted or unsubstituted $C_{1-4}$ alkylene group, the molecule containing at least one iodine atom and being metabolisable to products which are soluble in body fluids.

Where the group $R^3$ is not joined to $R^2$, the metabolic products will be $R^1COOH$, $R^3COOH$ and $R^2CHO$. Where $R^3$ and $R^2$ together form an alkylene group, the products will be $R^1COOH$ and $HOOC(R^3.R^2)CHO$.

$R^2$ conveniently is hydrogen or an optionally substituted $C_{1-6}$ aliphatic group, $C_{6-10}$ aryl group or $C_{7-20}$ araliphatic group.

Aliphatic groups may be straight or branched, saturated or unsaturated and include, for example, alkyl and alkenyl groups e.g. methyl, ethyl, isopropyl, butyl or allyl groups. Araliphatic groups include monocarbocyclic aryl-alkyl groups; for example benzyl groups. Aryl groups include mono- or bi-cyclic aryl groups, for example phenyl, tolyl or naphthyl groups. Heterocyclic groups include 5 or 6-membered heterocyclic groups preferably having one heteroatom, for example furyl, thienyl or pyridyl groups.

Possible substituents in the above hydrocarbon groups $R^1$, $R^2$ and $R^3$ include hydroxyl, etherified hydroxyl, esterified hydroxyl, etherified thiol, N-alkylamino, N-$C_{1-6}$-acylamino, N-$C_{1-6}$-acyl-N-$C_{1-6}$ alkylamino, carbamoyl and N-$C_{1-6}$ alkylcarbamoyl groups and halogen atoms. It should be noted that aromatic rings such as phenyl may carry $C_{1-6}$ alkyl groups, as in the tolyl group. Substituents may be present in combination and thus, for example, N-acyl and N-alkyl groups may carry hydroxy or etherified or esterified hydroxyl groups.

Etherified hydroxyl groups include $C_{1-5}$ alkoxy groups such as methoxy groups. Esterified hydroxyl groups include $C_{1-6}$ acyloxy groups such as acetoxy groups.

Halogen atoms include fluorine, chlorine, bromine and iodine. More than one halogen atom may be present in any particular group, as in the trifluoromethyl group. It is particularly preferred that the molecule as a whole carries several iodine atoms, for example at least three.

It is particularly preferred that at least one of the groups $R^1$ and $R^3$ is an iodinated phenyl group, preferably a triiodophenyl group. Such a group may be selected from the very wide range of such groups present in commercial carboxylic acid or amide X-ray contrast-agents. Such groups include 2,4,6-triiodophenyl groups having at the 3- and/or 5-positions groups selected from carbamoyl, N-alkylcarbamoyl or N-hydroxyalkylcarbamoyl, acylamino, N-alkyl-acylamino and acylaminomethyl groups. In such groupings, acyl groups will commonly be acetyl groups and N-alkylacylamino groups will commonly be N-methylacetamino groups. N-hydroxyalkylcarbamoyl groups will commonly comprise 1,3- or 2,3-dihydroxypropyl groups as the hydroxyalkyl moiety.

It is important that the contrast agent according to the invention is substantially water-insoluble and thus, when administered in particulate form, will be entrapped by the liver or spleen. It is possible for relatively hydrophilic groups, such as hydroxyl, to be present provided the remainder of the molecule is sufficiently lipophilic to ensure minimal overall water-solubility. However, after metabolic enzymolysis, it is important that the metabolic products have sufficient water-solubility at physiological pH to be excreted from the target organs. They should also themselves be physiologically acceptable.

We have found that particulate compounds according to the invention on intravenous administration appear to be captured by the reticuloendothelial system of the liver and spleen, the resulting accumulation of particles greatly assisting the imaging of these organs. On the other hand, the phagocytosing cells of the liver (Kupffer cells) contain lysosomes which possess a broad spectrum of hydrolytic enzymes including a number of esterases. Thus, once the particles are phagocytised, they enter the lysosomes and are converted into water-soluble products which are subsequently excreted. The relative rapidity of the conversion of the compounds into water-soluble products significantly decreases the risk of toxic reactions.

As compared with liposomes, the particles of solid contrast agent according to the invention have a very much higher iodine content. Thus, to achieve a desired level of contrast, as provided by a particular amount of iodine, a far smaller amount of material has to be used and the risk of producing lung emboli is greatly reduced. Furthermore, the particulate material according to the invention, which is commonly crystalline, is generally much more stable to storage than the previously proposed liposomes.

The compounds of the invention, due to their iodine content, provide excellent X-ray image enhancement. Due to the presence of the relatively heavy iodine atoms, the particles reflect ultrasound and can also be used in enhancement of ultrasound images.

The invention also provides injectable contrast media comprising a compound according to the invention in particulate form in suspension in a liquid for injection.

The mean particle size of the contrast agent will, in general, be within the range 0.002 to 7 microns, preferably 0.01 to 3 microns.

The injectable liquid may be any sterile physiologically acceptable liquid such as physiological saline which may usefully contain a physiologically acceptable stabilising agent such as polyvinylpyrrolidone. For example having a molecular weight about 30,000 daltons or a polysorbate, for example Polysorbate 80.

The contrast media may be used in the enhancement of X-ray and ultrasound images of the liver and/or spleen of a human or non-human animal subject, in which method they will be administered intravascularly, normally intravenously, prior to imaging.

The compounds according to the invention may be prepared in any convenient way. In general, the compounds will be formed by esterification of an acid of the formula $R^1COOH$ or a functional derivative thereof with a compound of the formula $X-CHR^2-O-COR^3$, where X is a hydroxyl group or a leaving group such as a halogen atom or a mesyloxy or tosyloxy group. Where X represents a leaving group, the functional derivative of the acid of formula $R^1COOH$ will normally be a salt such as the potassium salt. Such a reaction will normally be carried out in solution, for example in a polar solvent such as dimethylformamide. Esterification may also be achieved by reacting the compound $XCHR^2.O.COR^3$ in which X is OH with the acid $R^1COOH$, in the presence of a coupling agent such as a diimide e.g. dicyclohexyl-carbodiimide, or with an acid halide $R^1COHal$ where Hal is a halogen atom such as chlorine.

Where the two groups $R^1$ and $R^3$ are to be the same, esterification may be achieved by reacting a compound of the formula $R^2CHX_2$ where X is a leaving group, with a functional derivative of the acid $R^1COOH$ such as a salt.

The particulate form of the contrast agent according to the invention may advantageously be prepared by precipitation from solution in a water-miscible solvent such as ethanol by admixture with water, which may conveniently contain a stabilising agent such as polyvinylpyrrolidone, with vigorous agitation, e.g. using ultrasound. In this way, it is possible to obtain particles of mean diameter of the order of 1.0 microns. Mechanical crushing, for example to an appropriate particle size is also suitable. The particles may then be suspended in the liquid for injection referred to above.

The following Examples are given by way of illustration only:

General procedure for the synthesis of the alpha-chloroalkyl esters from the alpha-(arylthio) alkyl esters Sulfuryl chloride in dry dichloromethane (2M) is added dropwise at 0° C. to a solution of the alpha(arylthio)alkyl ester (1.0 equiv.) in dry dichloromethane (0.5M). The mixture is stirred at ambient temperature before cyclohexene (1.0 equiv.) in dry dichloromethane (2M) is added dropwise at 0° C. Stirring is continued for 1 hour at ambient temperature before the solvent is removed and the residue distilled under vacuum.

INTERMEDIATE 1

1-(Phenylthio)ethyl pivalate

1-Chloroethyl phenyl sulfide (11.0 g, 61.9 mmol) in dry DMF (110 ml) at 0° C. is added to a solution of pivalic acid (5.75 g, 56.3 mmol) and potassium t-butoxide (6.32 g, 56.3 mmol) in dry DMF (110 ml). The mixture is stirred at ambient temperature for 24 hours, before water is added and the product extracted into diethyl ether. The ether solution is washed with 1M sodium hydroxide and four times with brine, before it is dried (MgSO$_4$) and evaporated. Distillation gave 8.47 g (63%), b.p. 80° C. (0.06 mm Hg). 1H-NMR (DMSO-d6); delta=1.10 (s, (CH$_3$)$_3$); 1.46 (d, J=7 Hz, CH$_3$); 6.20 (q, J=7 Hz, CH); 7.3–7.5 ppm (m, 5H).

INTERMEDIATE 2

1-Chloroethylpivalate

The title compound is prepared from Intermediate 1 by the General Procedure detailed above.

Amount: SO$_2$Cl$_2$ (23.1 mmol, 1.1 equiv.). Reaction time: 2 hours. Yield: 49%. B.p. 40° C. (10 mm Hg). 1H-NMR (DMSO-d6): delta=1.16 (s, (CH$_3$)$_3$); 1.74 (d, J=6 Hz, CH$_3$); 6.55 ppm (q, J=6 Hz, CH).

INTERMEDIATE 3

(Phenylthio)methyl phenylacetate

Cesium carbonate (12.9 g, 39.6 mmol) is added to a solution of phenylacetic acid (5.40 g, 39.6 mmol) in dry DMF (60 ml). The mixture is stirred at 60° C. for 15 minutes and cooled to 0° C., before chloromethyl phenylsulfide (5.76 g, 36 mmol) is added dropwise. Stirring is continued at 0° C. for 30 minutes, then at ambient temperature for 3.5 hours and finally at 70° C. for 30 minutes, before water is added and the product extracted into diethyl ether. The ether solution is washed with 1M sodium hydroxide and 4 times with brine, dried (MgSO$_4$) and evaporated. The crude product is used in Intermediate 4 without further purification.

Yield: 8.10 g (87%). 1H-NMR (CDCl$_3$): delta=3.65 (s, CH$_2$S); 5.39 (s, CH$_2$); 7.2–7.4 ppm (m, 5H).

INTERMEDIATE 4

Chloromethyl phenylacetate

The title compound is prepared from Intermediate 3 by the General Procedure detailed above.

Amount: SO$_2$Cl$_2$ (19.0 mmol, 1.3 equiv.). Reaction time 2.5 hours. Yield (Overall for both stages): 1.46 g (50%). B.p. 68°–72° C. (0.001 mm Hg). 1H-NMR (CDCl$_3$): delta=3.69 (s, CH$_2$); 5.68 (s, CH$_2$Cl); 7.2–7.4 ppm (m, 5H).

INTERMEDIATE 5

(Phenylthio)methyl 2-thiophenecarboxylate

Cesium carbonate (8.14 g, 25.0 mmol) is added to a solution of phenylacetic acid (3.20 g, 25.0 mmol) in dry DMF (40 ml). The mixture is stirred at 60° C. for 25 minutes and cooled to 0° C., before chloromethyl phenylsulfide (3.60 g, 22.7 mmol) is added dropwise. Stirring is continued at 0° C. for 30 minutes, then at ambient temperature for 2 hours and finally at 70° C. for 15 minutes, before water is added and the product extracted into diethyl ether. The ether solution is washed with 1M sodium hydroxide and 4 times with brine, dried (MgSO$_4$) and evaporated. The crude product is used in Intermediate 6 without further purification.

Yield: 4.76 g (80%). 1H-NMR (CDCl$_3$): delta=5.59 (s, CH$_2$); 7.0–7.9 ppm (m, 8H).

INTERMEDIATE 6

Chloromethyl 2-thiophenecarboxylate

The title compound is prepared from Intermediate 5 by the General Procedure detailed above.

Amount: SO$_2$Cl$_2$ (18.6 mmol, 1.2 equiv.). Reaction time 1 hour. Yield: 83% B.p. 67°–69° C. (0.12 mbar). 1H-NMR (CDCl$_3$): delta=5.90 (s, CH$_2$); 7.0–8.0 ppm (m, 3H).

INTERMEDIATE 7

(Phenylthio)methyl 4-methoxy-3-methylbenzoate

Cesium carbonate (13.00 g, 40.0 mmol) is added to a solution of 4-methoxy-3-methyl benzoic acid (6.65 g, 40.0 mmol) in dry DMF (50 ml) at ambient temperature. The mixture is stirred at 65° C. for 20 minutes and cooled to 0° C., before chloromethyl phenylsulfide (5.76 g, 36 mmol) in dry DMF (10 ml) is added dropwise. Stirring is continued at 0° C. for 30 minutes, then at ambient temperature for 2 hours and finally at 70° C. for 1 hour, before water is added and the product extracted into diethyl ether. The ether solution is washed with 1M sodium hydroxide and 4 times with brine, dried (MgSO$_4$) and evaporated. The crude product is used in Intermediate 8 without further purification.

Yield: 9.60 g (83%). 1H-NMR (CDCl$_3$): delta=2.25 (s, CH$_3$); 3.85 (s, OCH$_3$); 5.63 (s, CH$_2$); 7.1–7.6 ppm (m, 8H).

INTERMEDIATE 8

Chloromethyl 4-methoxy-3-methylbenzoate

The title compound is prepared from Intermediate 7 by the General Procedure detailed above.

Amount: SO$_2$Cl$_2$ ( 30.0 mmol, 1.2 equiv.). Reaction time: 1.5 h. Yield: 90%. B.p. 100°–102° C./10 mm Hg. 1H-NMR (CDCl$_3$); delta=2.26 (s, CH$_3$); 3.87 (s, OCH$_3$); 5.94 (s, CH$_2$); 7.1–7.6 ppm (m, 3H).

INTERMEDIATE 9

1-Chloro-2-phenylethyl acetate

Made in accordance with the procedure given in Neuenschwander, Markus et. al., Helv. Chim. Acta, 61 (1978) 2047. The crude product is used in Example 12 without further purification.

Yield: 81%. 1H-NMR (CDCl$_3$): delta=1.98 (s, CH$_3$); 3.25 (m, CH$_2$); 6.52 (m, CH); 7.1–7.3 ppm (m, 5H).

EXAMPLE 1

Pivaloyloxymethyl 5-(N-acetylamino)-3-(N-acetyl-N-methylamino)-2,4,6-triiodobenzenecarboxylate Chloromethylpivalate (12.0 ml., 82.6 mmol) in dry DMF (130 ml) is added dropwise during 20 minutes at 50° C. to a solution of potassium 5-(N-acetylamino)-3-(N-acetyl-N-methylamino)-2,4,6-triiodobenzenecarboxylate (50.0 g, 75.0 mmol) and sodium iodide (600 mg, 4.0 mmol) in dry dimethylformamide (DMF) (750 ml). The precipitate is removed by filtration after stirring for 4 hours and the solvent removed at reduced pressure. The residue is dissolved in chloroform (400 ml) and washed four times with a saturated sodium hydrogen carbonate solution. After drying with magnesium sulfate the solvent is removed at reduced pressure and the residue recrystallized from acetone to give the title compound: 26.6 g (53%); m.p. 232°–234° C. 1H-N.M.R. (CDCl$_3$): delta=1.26 (s, C(CH$_3$)$_3$); 1.82 (s, N(CH$_3$)COCH$_3$); 2.22 (s, NCOCH$_3$); 3.08 (s, NCH$_3$); 6.02 (s, CH$_2$); 8.15 ppm (s, NH).

EXAMPLE 2

Di-[5-(N-acetylamino)-3-(N-acetyl-N-methylamino)-2,4,6-triiodophenylcarbonyloxy]methane Diiodomethane (300 microl, 3.8 mmol) is added dropwise during 5 minutes at 60° C. to a solution of potassium 5-(N-acetylamino)-3-(N-acetyl-N-methylamino)-2,4,6-triiodobenzenecarboxylate (5.0 g, 7.5 mmol) in dry DHF (75 ml). The precipitate is removed by filtration after stirring for 4 days and the solvent removed at reduced pressure. The residue is triturated with warm dioxane and filtered to give the title compound:

Yield 3.35 g (67%). 1H-N.M.R. (DMSO-d6): delta=1.70 (s, N(CH$_3$)COCH$_3$); 2.10 (s, NCOCH$_3$); 3.00 (s, NCH$_3$); 6.28 (s, CH$_2$); 6.28 (s, CH$_2$); 10.13 ppm (s, NH).

EXAMPLE 3

1-(Pivaloylyloxy)ethyl 5-(N-acetylamino)-3-(N-acetyl-N-methyl-amino)-2,4,6-triiodobenzenecarboxylate 1-Chloroethyl pivalate (0.40 g, 3.3 mmol) (Intermediate 2)-in dry DMF (6 ml) is added dropwise at 50° C. to a solution of potassium 5-(N-acetylamino)-3-(N-acetyl-N-methylamino)-2,4,6-triiodobenzenecarboxylate (2.00 g, 3.0 mmol) and sodium iodide (24 mg, 0.16 mmol) in dry DMF (30 ml). The precipitate is removed by filtration after stirring for 20 hours and the solvent is removed at reduced pressure. The residue is dissolved in chloroform (40 ml) and washed four times with a saturated sodium hydrogen carbonate solution. After drying with magnesium sulfate, the solvent is removed at reduced pressure to give the title compound:

Yield 1.85 g (81%). Purity by HPLC: 97%. Recrystallisation from acetone gives a purity of 98% (HPLC). 1H-NMR (DMSO-d6): delta=1.19 (s, (CH$_3$)$_3$); 1.59 (d, J=6 Hz, CH$_3$); 1.66 (s, N(CH$_3$)COCH$_3$); 2.04 (s, NCOCH$_3$); 2.96 (s, NCH$_3$); 7.06 ppm (m, CH).

EXAMPLE 4

1-(Acetyloxy)ethyl 5-(N-acetylamino)-3-(N-acetyl-N-methylamino)-2,4,6-triiodobenzenecarboxylate 1-Chloroethyl acetate (Neuenschwander, Markus et. al., Helv. Chim. Acta, 61 (1978) 2047) (4.38 g, 35.7 mmol) in dry DMF (50 ml) is added dropwise at 50° C. to a solution of potassium 5-(N-acetylamino)-3-(N-acetyl-N-methylamino)-2,4,6,-triiodobenzenecarboxylate (21.64 g, 32.5 mmol) and sodium iodide (0.26 g, 1.75 mmol) in dry DMF (320 ml). The precipitate is removed by filtration after stirring for 20 hours and the solvent is removed at reduced pressure. The residue is dissolved in chloroform (300 ml) and washed four times with a saturated sodium hydrogen carbonate solution. After drying with magnesium sulfate the solution is treated with activated carbon and the solvent is removed at reduced pressure to give the title compound:

Yield 20.61 g (89%). Purity by HPLC: 92%. Preparative HPLC gives a purity of 99%. 1H-NMR (DMSO-d6): delta=1.60 (d, J=6 Hz, CH$_3$); 1.66 (s, N(CH$_3$)COCH$_3$); 2.04 (s, NCOCH$_3$); 2.11 (s, OCOCH$_3$); 2.96 (s, NCH$_3$); 7.08 (q, J=6 Hz, CH); 10.11 ppm (s, NH).

EXAMPLE 5

Pivaloyloxymethyl 5-(N-acetylamino)-3-(methylaminocarbonyl)-2,4,6-triiodobenzenecarboxylate Chloromethylpivalate (7.62 g, 50.6 mmol) in dry DMF (84 ml) is added dropwise at 50° C. to a solution of potassium 5-(N-acetylamino)-3-(methylaminocarbonyl)-2,4,6-triiodobenzenecarboxylate (30.00 g, 46.0 mmol) and sodium iodide (0.37 g, 2.5 mmol) in dry DMF (450 ml). The precipitate is removed by filtration after stirring for 4 hours and the solvent is removed at reduced pressure. The residue is triturated and washed repeatedly in water and finally recrystallised from isopropanol.

Yield: 32.30 g (96%). Purity by HPLC: 98%. 1H-NMR (DMSO-d6): delta=1.20 (s, (CH$_3$)$_3$); 2.02 (s, CH$_3$CO); 2.73 ppm (d, J=5 Hz, NCH$_3$); 5.95 (s, CH$_2$); 8.4–8.7 (m, NHCH$_3$); 10.00 (s, NH).

EXAMPLE 6

(2-Thienylcarbonyloxy)methyl 5-(N-acetylamino)-3-(N-acetyl-N-methylamino)-2,4,6-triiodobenzenecarboxylate Chloromethyl 2-thiopbenecarboxylate (0.63 g, 3.6 mmol) (Intermediate 6) in dry DMF (70 ml) is added dropwise at 50° C. to a solution of cesium 5-(N-acetylamino)-3-(N-acetyl-N-methylamino)-2,4,6-triiodobenzenecarboxylate (3.00 g, 3.9 mmol) and sodium iodide (28 mg, 0.19 mmol) in dry DMF (45 ml). The precipitate is removed by filtration after stirring for 4 hours and the solvent is removed at reduced pressure. The residue is dissolved in chloroform (50 ml) and washed four times with a saturated sodium hydrogen carbonate solution. After drying with magnesium sulfate the solvent is removed at reduced pressure to give the title compound:

Yield 2.46 g (89%). Purity by HPLC: 97%. 1H-NMR (DMSO-d6): delta=1.66 (s, N(CH$_3$)COCH$_3$); 2.04 (s, NCOCH$_3$); 2.96 (s, NCH$_3$); 6.18 (s, CH$_2$); 7.2–8.1 (m, 3H); 10.11 ppm (s, NH).

EXAMPLE 7

Phenylacetyloxymethyl 5-(N-acetylamino)-3-(N-acetyl-N-methylamino)-2,4,6-triiodobenzenecarboxylate Chloromethyl phenylacetate (1.0 2 g, 5.5 mmol) (Intermediate 4) in dry DMF (50 ml) is added dropwise at 50° C. to a solution of cesium 5-(N-acetylamino)-3-(N-acetyl-N-methylamino)-2,4,6-triiodobenzenecarboxylate (3.80 g, 5.0 mmol) and sodium iodide (37 mg, 0.25 mmol) in dry DMF (70 ml). The precipitate is removed by filtration after stirring for 4 hours and the solvent is removed at reduced pressure. The residue is dissolved in chloroform (50 ml) and washed four times with a saturated sodium hydrogen carbonate solution. After drying with magnesium sulfate the solvent is removed at reduced pressure to give the title compound:

Yield 2.50 g (64%). Purity by HPLC: 97%. 1H-NMR (CDCl$_3$): delta=1.78 (s, N(CH$_3$)COCH$_3$); 2.21 (s, NCOCH$_3$); 3.05 (s, NCH$_3$); 3.72 (s, CH$_2$); 6.01 (s OCH$_2$); 7.30 (s C$_6$H$_5$); 7.79 ppm (s, NH).

EXAMPLE 8

4-Methoxy-3-methylbenzoyloxymethyl 5-(N-acetylamino)-3-(N-acetyl-N-methylamino)-2,4,6-triiodobenzenecarboxylate Chloromethyl 4-methoxy-3-methylbenzoate (Intermediate 8) (2.38 g, 11.0 mmol) in dry DMF (100 ml) is added dropwise at 50° C. to a solution of potassium 5-(N-acetylamino)-3-(N-acetyl-N-methylamino)-2,4,6-triiodobenzenecarboxylate (6.7 0 g, 10.0 mmol) and sodium iodide (75 mg, 0.50 mmol) in dry DMF (140 ml). The precipitate is removed by filtration after stirring for 4.5 hours and 16 hours at room temperature, and the solvent is removed at reduced pressure. The residue is dissolved in chloroform (100 ml) and washed four times with a saturated sodium hydrogen carbonate solution. After drying with magnesium sulfate the solvent is removed at reduced pressure to give the title compound:

Yield: 7.00 g (87%). Purity by HPLC: 93%. 1H-NMR (CDCl$_3$); delta=1.77 (s, N(CH$_3$)COCH$_3$); 2.20 (s, NCOCH$_3$); 2.26 (s, CH$_3$); 3.05 (s, NCH$_3$); 3.87 (s, OCH$_3$); 6.25 (s, OCH$_2$); 7.1–7.7 (m, 3H).

EXAMPLE 9

Pivaloyloxymethyl
3-(alpha-(3-(N-acetyl-N-methylamino)-5-(methylaminocarbonyl)-2,4,6-triiodobenzoylamino)
(N-acetylamino))-5-(N-(2-hydroxyethyl)
aminocarbonyl)-2,4,6-triiodobenzenecarboxylate Chloromethylpivalate (0.83 g, 5.5 mmol) in dry DMF (50 ml) is added dropwise at 50° C. to a solution of cesium
3-(alpha-(3-(N-acetyl-N-methylamino)-5-(methylaminocarbonyl) -2,4,6-triiodobenzoylamino)
(N-acetylamino))-5-(N-(2-hydroxyethyl)-aminocarbonyl)-2,4,6-triiodobenzenecarboxylate (7.00 g, 5.0 mmol) and sodium iodide (37 mg, 0.25 mmol) in dry DMF (70 ml). The solvent is removed at reduced pressure after stirring for 7 hours. The residue is triturated washed and filtered repeatedly, first with $CHCl_3$ and finally with $H_2O$.

Yield: 5.70 g (82%). Purity by HPLC: 95%. Anal. $C_{30}H_{31}I_6N_5O_6$: Calc. C 26.05%, H 2.26%, I 55.06%. Found C 25.98%, H 2.20%, I 54.90%. Both 1H- and 13C-NMR are similar for the title compound and the starting material (as free carboxylic acid) except for the carboxylic group itself which is esterified in the title compound. 1H-NMR (DMSO-d6) of the pivaloyloxymethyl group of the title compound is: delta=1.18 (s, $(CH_3)_3$) and 5.93 ppm (s, $CH_2$). The chemical shift of the $CH_2$ group is in accordance with Example 1 (delta=5.97 ppm in DMSO-d6) and not with the chloromethylpivalate which is the starting material (delta=5.84 ppm).

EXAMPLE 10

Acetyloxymethyl
5-(N-acetylamino)-3-(N-acetyl-N-methylamino)-2,4,6-triiodobenzenecarboxylate Chloromethylacetate (Neuenschwander, Markus et. al., Helv. Chim. Acta, 61 (1978) 2047) (2.30 g, 21.2 mmol) in dry DMF (100 ml) is added dropwise at 50° C. to a solution of cesium 5-(N-acetylamino)-3-(N-acetyl-N-methylamino)-2,4,6-triiodobenzenecarboxylate (13.4 g, 17.7 mmol) and sodium iodide (133 mg, 0.89 mmol) in dry DMF (210 ml). The precipitate is removed by filtration after stirring for 21 hours and the solvent is removed at reduced pressure. The residue is dissolved in chloroform (200 ml) and washed four times with a saturated sodium hydrogen carbonate solution. After drying with magnesium sulfate the solvent is removed at reduced pressure to give the title compound:

Yield 2.50 g (64%). Anal $C_{15}H_{15}I_3N_2O_6$: Calc. 25.74%, H 2.16%, N 4.00%. Found C 25.63%, H 2.19%, N 4.19%. 1H-NMR (DMSO-d6): delta=1.67 (s, $N(CH_3)COCH_3$); 2.05 (s, $NCOCH_3$); 2.14 (s, $OCOCH_3$); 2.98 (s, $MCH_3$) 5.94 (s, $CH_2$); 9.93 ppm (s, NH).

EXAMPLE 11

Acetyloxy-phenylmethyl
5-(N-acetylamino)-3-(N-acetyl-N-methylamino)-2,4,6-triiodobenzenecarboxylate Chloromethyl phenylacetate (Neuenschwander, Markus et. al., Helv. Chin. Acta, 61 (1978) 2047) (1.59 g. 8.6 mmol) in dry DMF (20 ml) is added dropwise at 50° C. to a solution of cesium 5-(N-acetylamino)-3-(N-acetyl-N-methylamino)-2,4,6-triiodobenzenecarboxylate (7.28 g, 9.6 mmol) and sodium iodide (64 mg, 0.42 mmol) in dry DMF (100 ml). The precipitate is removed by filtration after stirring for 20 hours and the solvent is removed at reduced pressure. The residue is dissolved in chloroform (200 ml) and washed twice with a saturated sodium hydrogen carbonate solution and twice with water. After drying with magnesium sulfate the solvent is removed at reduced pressure to give the title compound:

Yield 4.80 g (72%). 1H-NMR ($CDCl_3$): delta=1.78 (s, $N(CH_3)COCH_3$); 2.20 (s, $NCOCH_3$); 2.20 (s, $OCOCH_3$); 3.04 (s, $NCH_3$); 7.3-7.7 (m, 5H); 7.97 (s, CH); 8.39 ppm (s, NH).

EXAMPLE 12

1-Acetyloxy-2-phenylethyl
5-(N-acetylamino)-3-(N-acetyl-N-methylamino)-2,4,6-triiodobenzenecarboxylate 1-Chloro-2-phenylethyl acetate (Intermediate 9) (4.20 g, 21.1 mmol) in dry DMF (25 ml) is added dropwise at 50° C. to a solution of potassium 5-(N-acetylamino)-3-(N-acetyl-N-methylamino)-2,4,6-triiodobenzenecarboxylate (15.5 g, 23.2 mmol) and sodium iodide (158 mg, 1.0 mmol) in dry DMF (300 ml). The precipitate is removed by filtration after stirring for 21 hours and the solvent is removed at reduced pressure. The residue is dissolved in chloroform (200 ml) and washed four times with a saturated sodium hydrogen carbonate solution. After drying with magnesium sulfate the solvent is removed at reduced pressure to give the title compound:

Yield 6.70 g (40%). 1H-NMR ($CDCl_3$); delta=1.80 (s, N ($CH_3$) $COCH_3$); 2.20 (s, $NCOCH_3$); 3.05 (s, $NCH_3$); 3.30 (m, $CH_2$); 7.1-7.3 (m, 5H and CH).

Particle Preparation 1

Polyvinylpyrrolidone (1.00 g, MW 30,000 daltons) is dissolved in distilled water (25.0 ml) and filtered through a membrane filter with pore size 0.22 micrometer. A filtered solution of the product of Example 1 (0.1 g) in 96% ethanol (5.0 ml) is slowly added to the polyvinylpyrrolidone solution under vigorous ultrasonic stirring. The microparticles formed are centrifuged and washed repeatedly. The size and size distribution of the particles may be analyzed by light- and electron microscopy. The mean diameter is 1.0 micrometers which is also the diameter of the main fraction.

Particle Preparation 2

By mechanical crushing of the product of Example 1 particles with a mean diameter of 8 micrometers are obtained.

Particle Preparation 3

Polyvinylpyrrolidone (1.00 g, MW 40,000 daltons) is dissolved in distilled water (25.0 ml) and filtered through a membrane filter with pore size 0.22 micrometer. A filtered solution (0.22 micrometer) of the product of Example 2 (0.2 g) in methanol (5.0 ml) is slowly added to the polyvinylpyrrolidone solution under vigorous ultrasonic stirring. The microparticles formed are centrifuged and washed repeatedly. The size and size-distribution of the particles may be analysed by light- and electron microscopy. The mean diameter is 0.2 micrometer which is also the diameter of the main fraction.

Particle Preparation 4

Polyvinylpyrrolidone (1.00 g, MW 40,000 daltons is dissolved in distilled water (25.0 ml) and filtered through a membrane filter with pore size 0.22 micrometer. A filtered solution (0.22 micrometer) of the product of Example 3 (0.1 g) in 96% ethanol (5.0 ml) is slowly added to the polyvinylpyrrolidone solution under vigorous ultrasonic stirring. The microparticles formed are centrifuged and washed repeatedly. The size and size-distribution of the particles may be analysed by light- and electron microscopy. The mean diameter is 2.0 micrometers which is also the diameter of the main fraction.

Pharmaceutical Formulation 1

The particles of Particle Preparation 1 (1.0 g) are dispersed in a sterile filtered isotonic 0.9% sodium chloride/water for injection solution (100 ml) under vigorous stirring until a homogenous suspension is achieved.

Pharmaceutical Formulation 2

The particles of Particle Preparation 1 (1.0 g) are suspended in a sterile filtered 0.9% sodium chloride/water for injection solution (100 ml) containing Polyvinylpyrrolidone (4.0 g, MW 40,000), under vigorous stirring until a homogenous suspension is achieved.

Pharmaceutical Formulation 3

The particles of Particle Preparation 1 (1.0 g) are suspended in a sterile filtered 0.9% sodium chloride/water for injection solution (100 ml) containing polyvinylpyrrolidone (4.0 g, MW 40,000 daltons) adjusted to pH 7.4 by addition of 0.1N sodium hydroxide, under vigorous stirring until a homogeneous suspension is achieved.

Pharmaceutical Formulation 4

The particles of Particle Preparation 3 (1.0 g) are dispersed in a sterile filtered isotonic 0.9% sodium chloride/water for injection solution (100 ml) under vigorous stirring until a homogeneous suspension is achieved.

Pharmaceutical Formulation 5

The particles of Particle Preparation 3 (1.0 g) are suspended in a sterile filtered 0.9% sodium chloride/water for injection solution (100 ml) containing polyvinylpyrrolidone (4.0 g, MW 40,000 daltons) under vigorous stirring until a homogeneous suspension is achieved.

Pharmaceutical Formulation 6

The particles of Particle Preparation 3 (1.0 g) are suspended in a sterile filtered 0.9% sodium chloride/water for injection solution (100 ml) containing Polyvinylpyrrolidone (4.0 g, MW 40,000 daltons), adjusted to pH 7.4 by the addition of 0.1N sodium hydroxide, under vigorous stirring until a homogeneous suspension is achieved.

Pharmaceutical Formulation 7

The particles of Particle Preparation 4 (1.0 g) are dispersed in a sterile filtered isotonic 0.9% sodium chloride/water for infection solution (100 ml) under vigorous stirring until a homogeneous suspension is achieved.

Pharmaceutical Formulation 8

The particles of Particle Preparation 4 (1.0 g) are suspended in a sterile filtered 0.9% sodium chloride/water for injection solution (100 ml) containing Polyvinylpyrrolidone (4.0 g, MW 40,000 daltons) under vigorous stirring until a homogeneous suspension is achieved.

Pharmaceutical Formulation 9

The particles of Particle Preparation 4 (1.0 g) are suspended in a sterile filtered 0.9% sodium chloride/water for injection solution (100 ml) containing polyvinylpyrrolidone (4.0 g, MW 4 40,000 daltons), adjusted to pH 7.4 by addition of 0.1N sodium hydroxide, under vigorous stirring until a homogeneous suspension is achieved.

IN VITRO BIODEGRADATION

The powdered product of Example 1 is suspended in Seronorm (5 mg/ml) (Seronorm is a trade mark of Nycomed AS) at pH 7.4 and agitated at 37° C. As a control the experiment is also performed in phosphate buffered saline (PBS) at pH 7.4. At different time points samples are taken from the supernatant after centrifugation of the vial (4,000 rpm, 10 minutes). The release of Isopaque (5-(N-acetylamino)-3-(N-acetyl-N-methylamino)-2,4,6-triiodobenzenecarboxylic acid) is analysed by HPLC. More than 50% of the substance is hydrolysed during 6 hours and after 24 hours 90% is hydrolysed. In PBS no hydrolysis could be detected.

The powdered product of Example 3 is suspended in Seronorm (0.5 mg/ml) at pH 7.4 and agitated at 37° C. As a control the experiment is also performed in phosphate buffered saline (PBS) at pit 7.4. At different time points samples are taken from the supernatant after centrifugation of the vial (4,000 rpm, 10 minutes). The release of Isopaque (5-(N-acetylamino)-3-(N-acetyl-N-methylamino)-2,4,6-triiodobenzenecarboxylic acid) is analysed by HPLC. 4.1% of the substance is hydrolysed during 24 hours. In PBS 0.12% is hydrolysed during 72 hours.

The powdered product of Example 10 is suspended in Seronorm (0.5 mg/ml) at pH 7.4 and agitated at 37° C. As a control the experiment is also performed in phosphate buffered saline (PBS) at pH 7.4. At different time points samples are taken from the supernatant after centrifugation of the vial (4,000 rpm, 10 minutes). The release of Isopaque (5-(N-acetylamino)-3-(N-acetyl-N-methylamino)-2,4,6-triiodobenzenecarboxylic acid) is analysed by HPLC. The substrate is completely hydrolysed after 2 hours in Seronorm. In PBS 58% is hydrolysed during 72 hours.

The powdered product of Example 4 is suspended in Seronorm at (0.5 mg/ml) pH 7.4 and agitated at 37° C. As a control the experiment is also performed in phosphate buffered saline (PBS) at pH 7.4. At different time points samples are taken from the supernatant after centrifugation of the vial (4,000 rpm, 10 minutes). The release of Isopaque (5-(N-acetylamino)-3-(N-acetyl-N-methylamino)-2,4,6-triiodobenzenecarboxylic acid) is analysed by HPLC. 29% of the substance is hydrolysed during a 2 hour incubation and hydrolysis is complete after 24 hours in Seronorm. In PBS 34% was hydrolysed during 24 hours.

IN VIVO METABOLISM

The particles of Pharmaceutical Formulation 2 are injected intravenously into the tail vein of rats. The dose is 200 mg/kg, injection rate 1 ml/min and concentration 10 mg/ml. 30 minutes after injection about 35% of the dose is found in the liver. This uptake gives 0.9 mg I/g liver. The iodine content then gradually decreases to 7% after 6 hours. 24 hours p.i. no iodine can be detected in the liver. Bile and urine are sampled during the first 3 hours after injection. Excretion through these routes is 49 and 16% of injected dose respectively. All iodine is excreted as Isopaque (5-(N-acetylamino)- 3-(N-acetyl-N-methylamino)-2,4,6-triiodobenzenecarboxylic acid). During a 24 hour period all the iodine is excreted through urine or faeces in equal amounts (about 50% each).

The particles of Pharmaceutical Formulation 8 are injected intravenously into the tail vein of rats. The dose is 200 mg/kg, injection rate 1 ml/min and concentration 10 mg/ml. 30 minutes after injection more than 80% of the dose is found in the liver. This uptake gives 1.8 mg I/g liver. The iodine content then gradually decreases to 1–2% after 72 hours. One week p.i. no iodine can be detected in the liver. Bile and urine are sampled during the first 3 hours after injection. Excretion through these routes is 9.5 and 42% of injected dose respectively. All iodine is excreted as Isopaque (5-(N-acetylamino)-3-(N-acetyl-N-methylamino)-2,4,6-triiodobenzenecarboxylic acid). During a 7 day period all the iodine is excreted through urine or faeces in equal amounts (about 50% each).

We claim:

1. An injectable contrast medium having a reduced tendency to cause lung emboli following intravascular administration to a human or non-human animal subject of an X-ray or ultrasound image enhancing amount of the medium, wherein the medium comprises a water-insoluble iodinated ester of the formula (I):

in which
- $R^1$ is a substituted or unsubstituted $C_{1-20}$ aliphatic, $C_{7-20}$-araliphatic or $C_{6-20}$ aryl group or a $C_{1-20}$ heterocyclic group having one or more hetero atoms selected from O, S and N;
- $R^2$ is hydrogen or a substituted or unsubstituted aliphatic, aryl or araliphatic group; and
- $R^3$ is as defined above for $R^1$, and may be the same as or different from $R^1$;
- or $R^2$ and $R^3$ together represent a substituted or unsubstituted $C_{1-4}$ alkylene group,
- the molecule containing at least one iodine atom and being metabolizable to products which are soluble in body fluids;
- said ester being in particulate form in suspension in a liquid for injection and having a mean particle size within the range 0.01 to 3 microns.

2. An medium as claimed in claim 1 wherein, in the compound of formula I, $R^1$ and/or $R^3$ is an iodinated phenyl group.

3. An medium as claimed in claim 2 wherein $R^1$ and/or $R^3$ is an triiodophenyl group.

4. A process for the preparation of a medium as claimed in claim 1 comprising precipitation of the compound of formula (I) from solution in a water-miscible solvent by admixture with water, with agitation.

5. A process for the preparation of a medium as claimed in claim 1 comprising the steps of
   (i) mechanically crushing the solid compound of formula (I); and
   (ii) suspending the resulting particulate compound in a liquid for injection.

6. A method of enhancing an X-ray or ultrasound image of the liver and/or spleen of a human or non-human animal subject comprising the intravascular administration to the subject of an X-ray or ultrasound image enhancing amount of an injectable contrast medium, wherein the subject is at risk of developing lung emboli following said administration, the improvement comprising reducing the risk of developing lung emboli following administration of the medium, which medium comprises a water-insoluble iodinated ester of the formula (I)

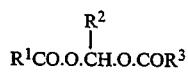

in which
- $R^1$ is a substituted or unsubstituted $C_{1-20}$ aliphatic, $C_{7-20}$-araliphatic or $C_{6-20}$ aryl group or a $C_{1-20}$ heterocyclic group having one or more hetero atoms selected from O, S and N;
- $R^2$ is hydrogen or a substituted or unsubstituted aliphatic, aryl or araliphatic group; and
- $R^3$ is as defined above for $R^1$, and may be the same as or different from $R^1$;
- or $R^2$ and $R^3$ together represent a substituted or unsubstituted $C_{1-4}$ alkylene group,
- the molecule containing at least one iodine atom and being metabolizable to products which are soluble in body fluids;
- said ester being in particulate form in suspension in a liquid for injection and having a mean particle size within the range 0.01 to 3 microns.

7. A medium as claimed in claim 1 wherein the compound of formula (I) is Pivaloyloxymethyl-5-(N-acetylamino)-3-(N-acetyl-N-methylamino)-2,4,6-triiodobenzenecarboxylate.

* * * * *